United States Patent
Wales et al.

(10) Patent No.: US 11,666,490 B2
(45) Date of Patent: Jun. 6, 2023

(54) MEDICAL SYSTEMS, DEVICES, AND RELATED METHODS

(71) Applicant: Boston Scientific Scimed, Inc., Maple Grove, MN (US)

(72) Inventors: Ryan V. Wales, Northborough, MA (US); Kira Sullivan, Sudbury, MA (US); Shawn Ryan, Littleton, MA (US); Jessica Louise Powers, Boston, MA (US); Joseph W. King, Franklin, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 150 days.

(21) Appl. No.: 17/185,188

(22) Filed: Feb. 25, 2021

(65) Prior Publication Data

US 2021/0267813 A1      Sep. 2, 2021

Related U.S. Application Data

(60) Provisional application No. 62/982,926, filed on Feb. 28, 2020.

(51) Int. Cl.
*A61F 13/20* (2006.01)
*A61F 13/26* (2006.01)
*A61F 13/84* (2006.01)

(52) U.S. Cl.
CPC ........ *A61F 13/2002* (2013.01); *A61F 13/266* (2013.01); *A61F 13/8405* (2013.01); *A61B 2217/005* (2013.01); *A61F 2013/2014* (2013.01)

(58) Field of Classification Search
CPC .............. A61F 13/2002; A61F 13/2005; A61F 13/2008; A61F 13/2011; A61F 13/2017; A61F 2013/2014; A61F 13/34; A61F 13/00068; A61M 25/0668; A61M 1/915; A61M 1/916
See application file for complete search history.

(56) References Cited

U.S. PATENT DOCUMENTS

| | | | |
|---|---|---|---|
| 4,525,166 A * | 6/1985 | Leclerc | A61M 1/68 604/313 |
| 8,791,315 B2 | 7/2014 | Lattimore et al. | |
| 9,078,786 B1 * | 7/2015 | Miller | A61F 13/2028 |

(Continued)

FOREIGN PATENT DOCUMENTS

| | | |
|---|---|---|
| DE | 102008061536 A1 | 6/2010 |
| DE | 102014224012 A1 | 5/2016 |

(Continued)

OTHER PUBLICATIONS

International Search Report and Written Opinion in International Application No. PCT/US2021/019600, dated Jun. 18, 2021 (13 pages).

*Primary Examiner* — Catharine L Anderson
*Assistant Examiner* — Arjuna P Chatrathi
(74) *Attorney, Agent, or Firm* — Bookoff McAndrews, PLLC

(57) ABSTRACT

In one example, a medical system may comprise a delivery tube configured to couple to a vacuum source and provide negative pressure to a distal portion of the delivery tube; and a porous body at a distal portion of the delivery tube, the porous body including a first section and a second section removable from the first section.

20 Claims, 2 Drawing Sheets

(56) References Cited

U.S. PATENT DOCUMENTS

| | | | |
|---|---|---|---|
| 10,058,413 B2 | 8/2018 | Heiss | |
| 10,779,928 B2 | 9/2020 | Heiss | |
| 2006/0079852 A1 | 4/2006 | Bubb et al. | |
| 2010/0228184 A1* | 9/2010 | Mavani | A61B 17/0057 604/35 |
| 2011/0270205 A1* | 11/2011 | Odermatt | A61F 13/15211 604/374 |
| 2013/0023840 A1* | 1/2013 | Loske | A61M 1/92 604/319 |
| 2013/0123723 A1* | 5/2013 | Tout | A61F 13/00068 604/319 |
| 2013/0190706 A1* | 7/2013 | Kleiner | A61M 1/90 604/319 |
| 2016/0022500 A1* | 1/2016 | Tumey | A61F 13/00008 604/319 |
| 2016/0206478 A1* | 7/2016 | Nordbo | A61F 13/00068 |
| 2019/0262182 A1* | 8/2019 | Collinson | A61M 1/916 |
| 2019/0336345 A1* | 11/2019 | Bannwart | A61F 13/148 |
| 2020/0000985 A1* | 1/2020 | Seddon | A61M 1/79 |
| 2020/0276056 A1* | 9/2020 | Leeds | A61F 13/00068 |

FOREIGN PATENT DOCUMENTS

| | | | | |
|---|---|---|---|---|
| EP | 2394677 A1 | | 12/2011 | |
| EP | 2786713 A1 | * | 10/2014 | A61B 17/1114 |
| EP | 2851102 A1 | | 3/2015 | |
| WO | 2014044400 A1 | | 3/2014 | |
| WO | 2019059893 A1 | | 3/2019 | |
| WO | WO-2019059893 A1 | * | 3/2019 | A61F 13/00068 |

\* cited by examiner

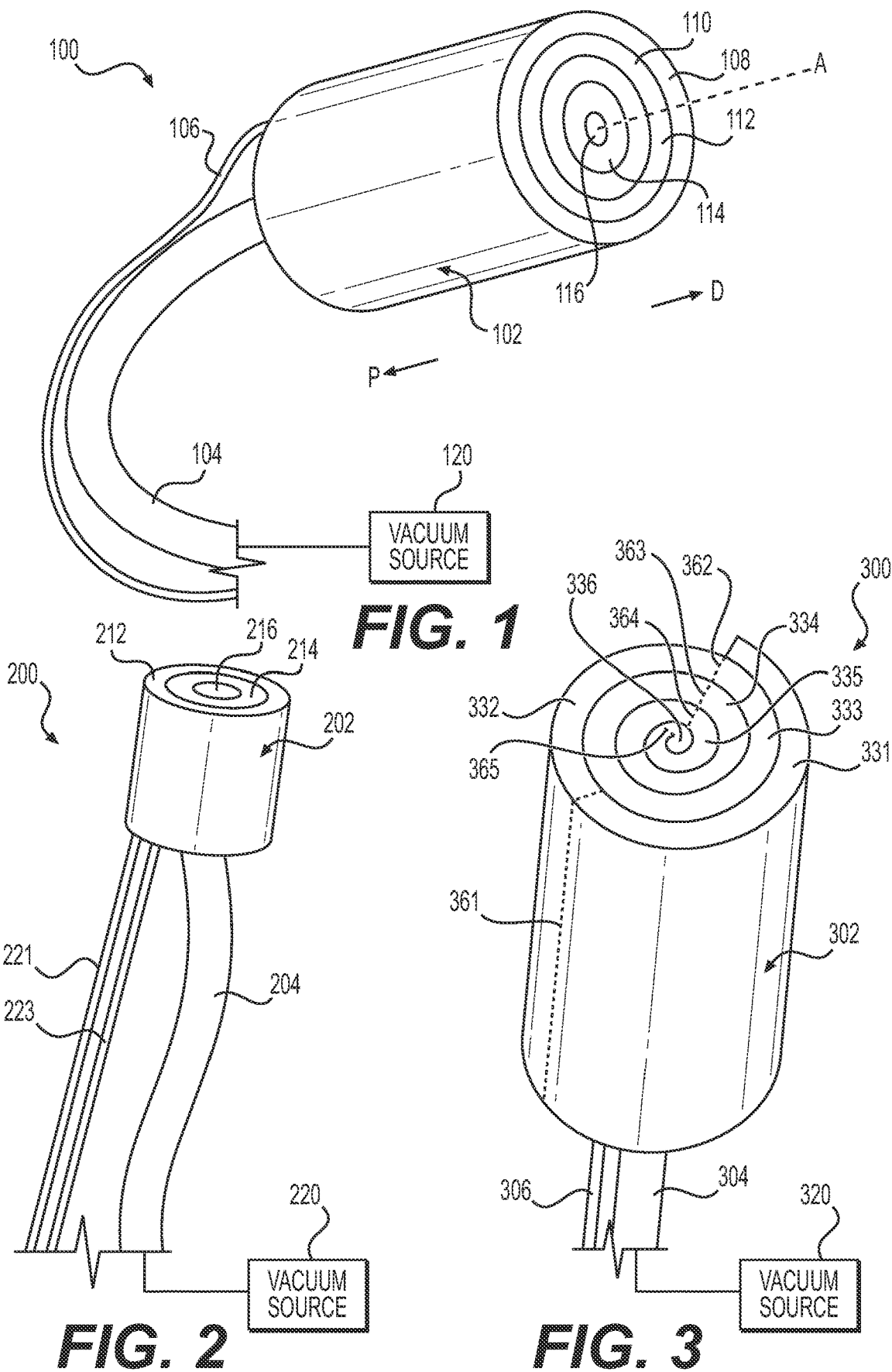

MEDICAL SYSTEMS, DEVICES, AND RELATED METHODS

CROSS-REFERENCE TO RELATED APPLICATIONS

This application claims the benefit of priority from U.S. Provisional Application No. 62/982,926, filed on Feb. 28, 2020, which is incorporated by reference herein in its entirety.

TECHNICAL FIELD

This disclosure generally relates to medical systems, devices, and related methods that may be used to treat a subject. Aspects of the disclosure relate to medical systems, devices, and methods for endoscopic medical procedures, such as applying negative pressure to tissue for wound treatment.

BACKGROUND

Endoscopic and open surgical procedures of the gastrointestinal (GI) tract include, for example, colonic resection, bariatric surgery, esophagectomy, gastric bypass, and sleeve gastrectomy, among others. These procedures may result in perforation, post-surgical leaks, or other wounds of the tract. Limited treatment options exist for managing such wounds, which have significant morbidity and mortality rates. Options include surgical re-operation and endoscopic placement of a stent or clips. Surgery is relatively invasive and also has high morbidity and mortality rates. Endoscopic stent placement is a less invasive option. The placed stent, however, can migrate from the intended location and/or wall off infection at the treatment site, inhibiting drainage.

The systems, devices, and methods of this disclosure may rectify some of the deficiencies described above or address other aspects of the art.

SUMMARY

Examples of the disclosure relate to, among other things, systems, devices, and methods for performing one or more medical procedures with the medical systems and devices. Each of the examples disclosed herein may include one or more of the features described in connection with any of the other disclosed examples.

In one example, a medical system may comprise a delivery tube configured to couple to a vacuum source and provide negative pressure to a distal portion of the delivery tube; and a porous body at a distal portion of the delivery tube, the porous body including a first section and a second section removable from the first section.

In other aspects of the disclosure, the medical system may include one or more of the features below. The second section may extend circumferentially around a radially-outermost surface of the first section, and the radially-outermost surface may be radially-outermost from a central longitudinal axis of the porous body. The system may further comprise a string coupled to the second section and extending from the porous body to a proximal portion of the delivery tube. The porous body may further comprise a third section extending circumferentially around a radially-outermost surface of the second section, and the radially-outermost surface of the second section may be radially-outermost from a central longitudinal axis of the porous body. The system may further comprise a first string coupled to the second section and extending from the porous body to a proximal portion of the delivery tube; and a second string coupled to the third section and extending from the porous body to the proximal portion of the delivery tube. The delivery tube may be coupled to a vacuum source, the porous body may be cylindrical, and a central longitudinal axis of the porous body may be longitudinally aligned with a central longitudinal axis of the delivery tube. The system may further comprise a flexible overtube coupled to the second section, and the delivery tube may extend through a lumen of the flexible overtube.

In other aspects of the disclosure, the medical system may include one or more of the features below. The first section may be cylindrical and the second section may wrap around the first section. The first section and the second section may be separated by perforations. The first section may be cylindrical and may include a central longitudinal axis; the second section may extend circumferentially around a radially-outermost surface of the first section, the radially-outermost surface may be radially-outermost from the central longitudinal axis of the first section; and the second section may be cylindrical and include a lumen extending through the central longitudinal axis configured to receive the first section. A layer of mesh, adhesive, or agent may be positioned between the first section and the second section. The system may further comprise a cylindrical overtube extending around the delivery tube and the porous body, and the overtube may be configured to cover the porous body and the delivery tube. The system may further comprise a string coupled to the second section and the third section, the string may extend from the sponge to a proximal portion of the delivery tube, and wherein the string includes: a first portion coupled to the second section and the third section, wherein the first portion has a length longer than a length of the delivery tube; and a second portion coupled to the third section and extending proximally to the proximal portion of delivery tube. The first section, the second section, and the third section may be concentric and may have different thicknesses measured orthogonal to a central longitudinal axis of the porous body. The first string may be a different color than the second string.

In another aspect, a medical device may comprise a porous body including at least one perforation; a negative pressure conduit having an opening formed therein that is in fluid communication with the porous body, wherein the negative pressure conduit is configured to apply a negative pressure to the porous body; and a string coupled to the porous body and extending from the porous body to a proximal portion of the conduit. The porous body may be configured to separate into separate sections when the string is pulled proximally.

In other aspects of the disclosure, the device may include one or more of the features below. The at least one perforation may extend longitudinally along the porous body. The conduit may be longitudinally aligned with a central cylindrical section of the porous body, and the at least one perforation may extend parallel to a longitudinal axis of the central section. The at least one perforation may include a first perforation and a second perforation; and the first perforation may be closer to a central longitudinal axis of the porous body than the second perforation.

In another aspect, a method of performing a medical procedure may comprise: positioning a porous body adjacent to tissue of a target site; applying a negative pressure to the porous body; and pulling a string coupled to the porous body proximally to remove a first section of the porous body while a second section of the porous body remains positioned at the target site.

It may be understood that both the foregoing general description and the following detailed description are exemplary and explanatory only and are not restrictive of this disclosure, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

FIG. 1 illustrates a perspective view of a distal portion of an exemplary medical device, according to aspects of this disclosure.

FIG. 2 illustrates a perspective view of a distal portion of an exemplary medical device, according to aspects of this disclosure.

FIG. 3 illustrates a perspective view of a distal portion of an exemplary medical device, according to aspects of this disclosure.

DETAILED DESCRIPTION

Figure 4A:
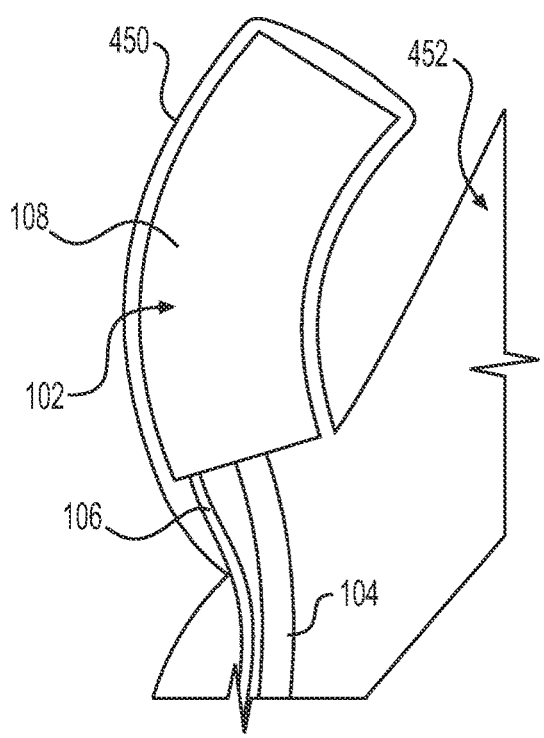
FIGS. 4A-4D illustrate views of a medical device in various stages of usage in a subject, according to aspects of the disclosure.

The terms "proximal" and "distal" are used herein to refer to the relative positions of the components of an exemplary medical system and exemplary medical devices. When used herein, "proximal" refers to a position relatively closer to the exterior of the body or closer to a medical professional using the medical system or medical device. In contrast, "distal" refers to a position relatively further away from the medical professional using the medical system or medical device, or closer to the interior of the body. Proximal and distal directions are labeled with arrows marked "P" and "D", respectively, throughout the figures. As used herein, the terms "comprises," "comprising," "having," "including," or other variations thereof, are intended to cover a non-exclusive inclusion, such that a system, device, or method that comprises a list of elements does not include only those elements, but may include other elements not expressly listed or inherent thereto. Unless stated otherwise, the term "exemplary" is used in the sense of "example" rather than "ideal." As used herein, the terms "about," "substantially," and "approximately," indicate a range of values within +/−10% of a stated value.

Endoluminal vacuum therapy (EVAC) has been proposed. In EVAC, negative pressure is delivered to the wound site in the GI tract, for example through a nasogastric tube having a sponge at its terminal end. The sponge is placed endoscopically into the perforation, leak, or other wound. Negative pressure then is applied. Devices and systems suited for EVAC are limited, however.

Embodiments of this disclosure include devices, systems, and methods for endoluminal vacuum therapy (EVAC). In examples, EVAC includes endoluminal placement of a sponge or other like material into the wound site, including a perforation, cyst, a leak, an anastomosis, etc. Placement of the material may be via a catheter, scope (endoscope, bronchoscope, colonoscope, gastroscope, duodenoscope, etc.), tube, or sheath, inserted into the GI tract via a natural orifice. The orifice can be, for example, the nose, mouth, or anus, and the placement can be in any portion of the GI tract, including the esophagus, stomach, duodenum, large intestine, or small intestine. Placement also can be in other organs reachable via the GI tract.

Reference will now be made in detail to examples of this disclosure described above and illustrated in the accompanying drawings. Wherever possible, the same reference numbers will be used throughout the drawings to refer to the same or like parts.

FIG. 1 illustrates a perspective view of an exemplary medical device 100 including a sponge 102, that may be used to help the healing of an internal wound, anastomosis, or the like, in a subject. Sponge 102 may be substantially cylindrical and may be attachable, e.g., coupled, to a vacuum tube 104. A central longitudinal axis A of sponge 105 may be aligned with a central longitudinal axis (also shown as axis A in FIG. 1) of vacuum tube 104. Sponge 102 may be sized in accordance with a patient's anatomy and may include a lumen or recess (not shown) to receive vacuum tube 104. The recess may be in a proximal end of sponge 102. In some examples, sponge 102 may include a curved, radially-outermost surface 119. Sponge 105 may be flexible and configured to move through tortuous pathways of body lumens of a patient.

Sponge 102 may include a plurality of concentric sections 116, 114, 112, 110, 108. Each section 116, 114, 112, 110, 108 may be separate from each other section 116, 114, 112, 110, 108. A central section 116 may be shaped as a cylinder and may be directly coupled to vacuum tube 104. For example, section 116 may have a lesser length than sections 114, 112, 110, and 108, to accommodate a distal portion of tube 104 within sponge 102. Each of the other sections 114, 112, 110, 108 may extend circumferentially around the central section 116 forming concentric, ring-like cylindrical sections 114, 112, 110, 108 that are nested within one another. In some examples, each section 116, 114, 112, 110, 108 of sponge 102 may be a different distance from central longitudinal axis A, and each section 116, 114, 112, 110, 108 may extend longitudinally in the direction of central longitudinal axis A. In some examples, sections 116, 114, 112, 110, 108 may have the same thickness measured in a direction perpendicular to longitudinal axis A, and sections 114, 112, 110, 108 may have the same length measured parallel to longitudinal axis A. In other examples, sections 116, 114, 112, 110, 108 may have different thicknesses and/or may have different lengths. In some examples, sponge 102 may include five sections (shown in FIG. 1), and in other examples, sponge 102 may include 2, 3, 4, 6, 7, 8, 9, or any other suitable number of sections. Each section 114, 112, 110, 108 may contact the radially-outer surface from longitudinal axis A of the adjacent section 116, 114, 112, 110, respectively.

Sections 116, 114, 112, 110, 108 may be configured to move relative to each other such that a section 116, 114, 112, 110, 108 may be moved in the proximal-distal direction relative to the other sections 116, 114, 112, 110, 108 with no or minimal movement of the other sections 116, 114, 112, 110, 108. In some examples, a layer of mesh, adhesive, or agent may be positioned between each section 116, 114, 112, 110, 108 and the adjacent section 116, 114, 112, 110, 108, which may facilitate removal of each section 116, 114, 112, 110, 108. In other examples, any other suitable material, capable of coupling adjacent sections together yet permitting them to release from one another upon a suitable force, may be used between adjacent sections. Such materials can include a suitable adhesive layer sandwiched between adjacent sections. In some examples, a medicament may be layered/sandwiched between adjacent sections and may be configured to release from sponge 102 when the radially-outer layer from the longitudinal axis of sponge 102 is removed and exposes the layer of medicament. In some examples, sponge 102 may be sized to fill a wound region 450 with a radius of between approximately 1 cm and 7 cm, and/or a wound region 450 with a depth of between approximately 1 cm and 7 cm.

In embodiments of this disclosure, sponge 102 may be any suitable biocompatible material that may absorb liquids and/or permit liquid to pass therethrough via negative pressure. The material may be flexible, compressible, porous, hydrophilic, sterile, biodegradable, and/or disposable. The sponge material may be an open-cell foam having pores and channels therein. Suitable materials include polyurethanes, esters, ethers, composite materials, and any medical-grade material.

A string or suture 106 may be coupled to sponge 102 and may extend from sponge 102 proximally to a proximal portion of medical device 100. String 106 may be coupled to each section 108, 110, 112, 114 except central section 116. A length of string 106 longer than the length (measured longitudinally) of medical device 100 may be between each point at which string 106 is coupled to each section 108, 110, 112, 114, which may allow each section 108, 110, 112, 114 to be pulled proximally the entire length of medical device 100 without pulling any other section 108, 110, 112, 114. The length of string 106 between each point of string 106 that is coupled to each section 108, 110, 112, 114 may be sandwiched between adjacent sections 108, 110, 112, 114. For example, string 106 may be coupled to section 108, then coupled to section 110, then coupled to section 112, and then coupled to section 114; and the length of string between each point at which string 106 is coupled to each section may be positioned between sections (such as wound around a section, etc.). This additional length of string 106 between each section 108, 110, 112, 114 is configured to allow the user to pull section 108 proximally out of a patient's body without removing the rest of sections 110, 112, 114, 116; and then proceed to pull the next radially-outermost section (in this case, section 110) proximally out of a patient's body without moving the rest of sections 112, 114, 116; and so forth.

In some examples, medical device 100 may include a single, separate string coupled to each section 108, 110, 112, 114; and thus four strings 106 would extend proximally from sponge 102. In some examples, medical device 100 may include a single string 106 coupled to each section 108, 110, 112, 114, and each of the strings 106 may be a different color so the user removing the layers (sections 108, 110, 112, 114) of sponge 102 may identify which layer is being removed. In other examples, string 106 may be replaced with a wire, a tether, or an extrusion. In some examples, string 106 may be replaced with a series of concentric tubes extending from sponge 102 to a proximal portion of medical device 100, with each tube coupled to a single section 108, 110, 112, 114. In this example, the tubes would be flexible and configured to move through a patient's body.

Vacuum tube 104 may be cylindrical with a central lumen (not shown) extending along central longitudinal axis A of vacuum tube 104. Vacuum tube 104 may have a length and width configured to extend through a working channel of an endoscope or other medical delivery device, and may be flexible. In some examples, vacuum tube 104 may include one or more holes at a distal portion of vacuum tube 104, including portions within sponge 102. Vacuum tube 104 may be coupled to a vacuum source 120 at a proximal portion of vacuum tube 104. Vacuum source 120 may supply negative air pressure to vacuum tube 101. Vacuum tube 104 may be coupled to at least central section 116 of sponge 102, and may supply negative air pressure to sponge 102. In some examples, vacuum tube 104 may extend through central portion 116 of sponge 102. Vacuum tube 104 may be received within a recess of a proximal portion of sponge 102, and in some examples vacuum tube 104 may be coupled to sponge 102 via an adhesive, a suture, a thread, and/or other attachment means.

In some examples, medical device 100 may include an overtube (not shown) which may extend over vacuum tube 104 and sponge 102. The overtube may compress sponge 102 such that the radially-outermost surface from longitudinal axis A of sponge 102 is smaller than when sponge 102 is positioned outside of the overtube. An overtube may facilitate movement of medical device 100 through a working channel of an endoscope or other medical device. In addition, an overtube may prevent unwanted contact of sponge 102 with tissue of the patient.

FIG. 2 shows a perspective view of a distal portion of an alternative embodiment of a medical device 200. Medical device 200 may have any of the features described hereinabove with regard to medical device 100. Medical device 200 may include a vacuum tube 204 and a sponge 202, and may be coupled to a vacuum source 220 at a proximal portion of medical device 200. In the same manner described hereinabove with regard to sponge 102, sponge 202 includes concentric, cylindrical sections 212, 214, 216. At least central section 216 is directly coupled to vacuum tube 204, section 214 is coupled to a first string 223, and section 212 is coupled to a second string 221. Each of first string 223 and second string 221 may extend from sponge 202 to a proximal portion of medical device, and may be configured to be moved proximally to remove a section 212, 214 of sponge 202 from a body of a patient. In some examples (shown in FIG. 2), strings 221, 223 may be coupled to each of sections 212, 214, respectively, at a proximal portion of each section 212, 214. Strings 221, 223 may extend proximally outside of vacuum tube 204.

FIG. 3 shows a perspective view of a distal portion of another embodiment of a medical device 300. Medical device 300 may have any of the features described hereinabove with regard to medical devices 100, 200. Medical device 300 may include a vacuum tube 304, a sponge 302, and a string 306. Vacuum tube 304 may be coupled to a vacuum source 320 at a proximal portion of vacuum tube 304. Sponge 302 may include several sections 331, 332, 333, 334, 335, 336, and the sections 331, 332, 333, 334, 335 may be coiled around central section 336. Each section 331, 332, 333, 334, 335 may be wrapped around the section or sections adjacent to it and/or radially inward of it, and sections 331, 332, 333, 334, 335, 336 may form a spiral about a central longitudinal axis of sponge 302. In some examples, a single, rectangular sponge may be perforated to divide the sponge into sections 331, 332, 333, 334, 335, 336, and then the rectangular sponge may be rolled around a central section (such as section 336 in FIG. 3) to form sponge 302. String 306 may be coupled to each section 331, 332, 333, 334, 335, 336, with portions of string that are the length of medical device 300 between each point of coupling string 306 to each respective section 331, 332, 333, 334, 335, 336.

Adjacent sections 331, 332, 333, 334, 335, 336 may be separated by perforations 361, 362, 363, 364, 365. Perforations 361, 362, 363, 364, 365 may be configured to allow sections 331, 332, 333, 334, 335, 336 to separate from each other when a user pulls string 306 proximally. For example, when a user first pulls string 306 proximally, section 331 may be pulled proximally and perforation 361 may allow section 331 to separate from section 332 without moving or minimally moving section 332 or any other section. The user may then continue to pull string 306 proximally to separate section 332 from section 333, then separate section 333 from section 334, etc. In other examples, individual strings 306 may be coupled to each section 331, 332, 333, 334, 335, 336 such that a user needs to pull one string to remove section 331, then a second string to remove section 332, etc. In some examples (not shown), central section 336 may be a separate sponge from sponge 302. Perforations 361, 362, 363, 364, 365 may extend longitudinally, substantially parallel to axis A. In other examples, perforations 361, 362, 363, 364, 365 may be replaced by a thinner region or otherwise weakened region between each section 331, 332, 333, 334, 335, 336, permitting release of adjacent sections 331, 332, 333, 334, 335, 336 upon application of a suitable force. Each section 331, 332, 333, 334, 335, 336 may be any suitable size. In some examples, each section 331, 332, 333, 334, 335, 336 may extend 360° circumferentially around a central longitudinal axis of vacuum tube 304. In other examples, each section 331, 332, 333, 334, 335, 336 may extend less than 360° circumferentially around the axis, like section 331 shown in FIG. 3. Perforations 361, 362 may provide a means for a user to select the size of sponge 302 prior to insertion of sponge 302 into a body of a patient. Also, a layer of mesh, adhesive, agent, or other material can be used between adjacent sections 331, 332, 333, 334, 335, 336, as described hereinabove.

Reference will now be made in detail to methods of operating medical devices 100, 200, 300. Although FIGS. 4A-4D show the operation of medical device 100, any of the medical devices 100, 200, 300 may operate by the same method described herein below with regard to medical device 100.

FIGS. 4A-4D show side views of medical device 100 in use within a body lumen 452 of a patient (e.g. a portion of the gastrointestinal tract) to treat a wound region 450. To position medical device 100 at a wound region 450 within a body of a patient, a user may insert an endoscope (or other medical device) into the patient and locate wound region 450 by visualizing the wound region 450 using an image sensor (not shown) at a distal end of the endoscope. Once the endoscope is positioned proximate to wound region 450, the user may insert medical device 100 into a working channel of the endoscope and move medical device 100 distally through the working channel. In other examples, medical device 100 may be positioned within a working channel proximate to the distal end of the endoscope prior to inserting the endoscope into the body of the patient. In some examples, an overtube may be positioned between medical device 100 and a working channel, and the overtube may prevent excessive bending, twisting, or other shape distortion of medical device 100 within the working channel while the user moves medical device 100 distally through the working channel. In other examples, a user may not use an endoscope and may insert medical device 100 into the body of the patient directly and not within a working channel of a separate medical device.

With a distal portion of the endoscope positioned proximate to wound region 450, the user may move medical device 100 distally out of the working channel and position sponge 102 within wound region 450. The flexibility, compressibility, and shape of sponge 102, and the flexibility of vacuum tube 104 may facilitate maneuvering medical device 100 within wound region 450. In some examples, sponge 102 may bend, twist, and/or change shape to conform to the shape of wound region 450. The user may then activate vacuum source 120 to supply negative pressure to sponge 102 through vacuum tube 104, which may pull portions of wound region 450 towards sponge 102. Once medical device 100 is positioned within wound region 450 and vacuum pressure is supplied to sponge 102, the user may then leave sponge 102 and vacuum tube 104 positioned within the body of the patient for approximately 48-72 hours. The negative pressure applied to sponge 102 may also remove fluid and other material from the wound region 450. In other examples, sponge 102 may be left within the patient's body for any other period of time. Vacuum tube 104 may remain within the body of the patient during treatment, and may extend out of the patient to vacuum source 120 through the patient's rectum, mouth, nose, other bodily orifice, or other opening in the patient's body such as an incision, etc. In some examples, an overtube may also remain within the patient's body during treatment and may cover a portion of sponge 102 outside of the wound region 450.

Figure 4B:
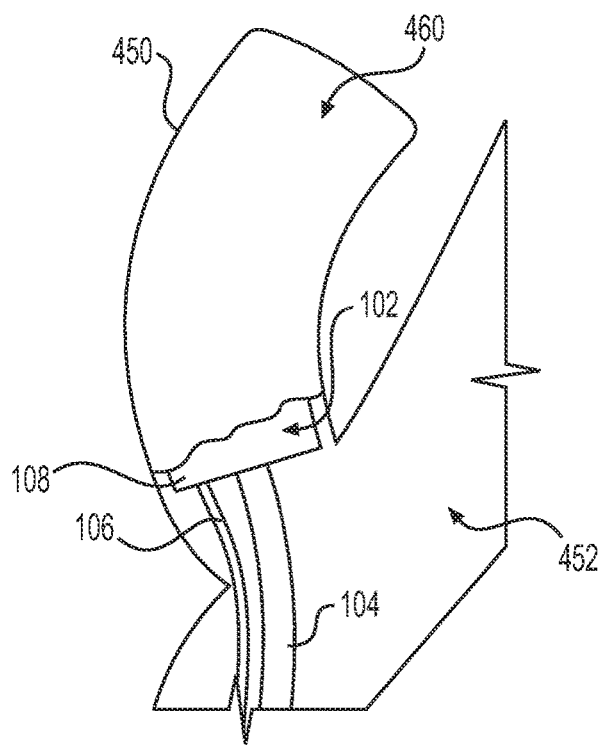

As wound region 450 heals, wound region 450 may shrink and become smaller. When a user would like to remove a section of sponge 102 (such as after 48-72 hours has passed since the initial positioning of sponge 102 within wound region), the user may first disconnect vacuum tube 104 from vacuum source 120 and supply saline 460 to vacuum tube 104 in order to deliver saline 460 to wound region 450. FIG. 4B illustrates saline 460 deployed within wound region 450. Although saline 460 is shown in FIG. 4B, any suitable liquid known in the art may be used to fill wound region 450 to facilitate removal of portions of sponge 102. Saline 460 may facilitate release of sponge 102 from the walls of wound region 450. Once saline 460 is deployed, a user may position a rigid tool 455 within the patient such that a distal end of rigid tool 455 is contacting section 110 of sponge 102. Rigid tool 455 may prevent proximal movement of section 110 when the user pulls section 108 proximally. Rigid tool 455 may be a metal wire, tube, rod, or any other suitable relatively rigid member.

Figure 4C:
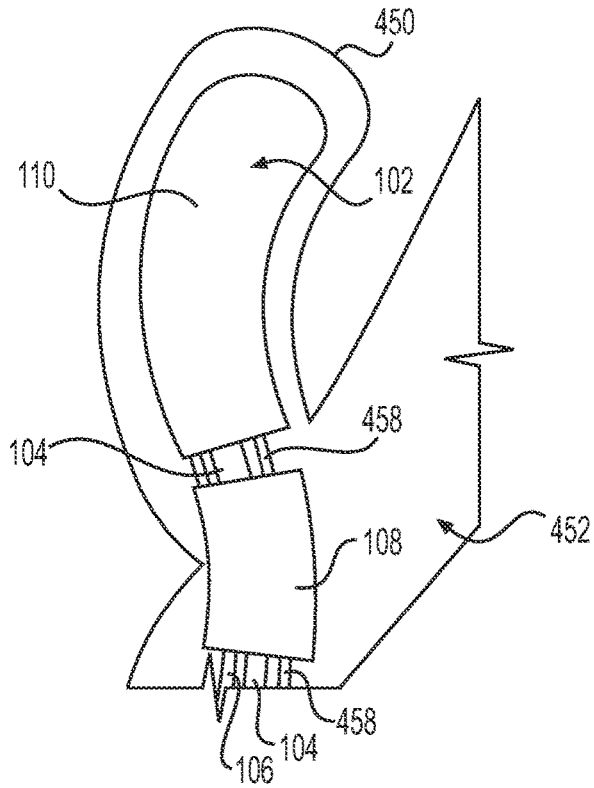
Figure 4D:
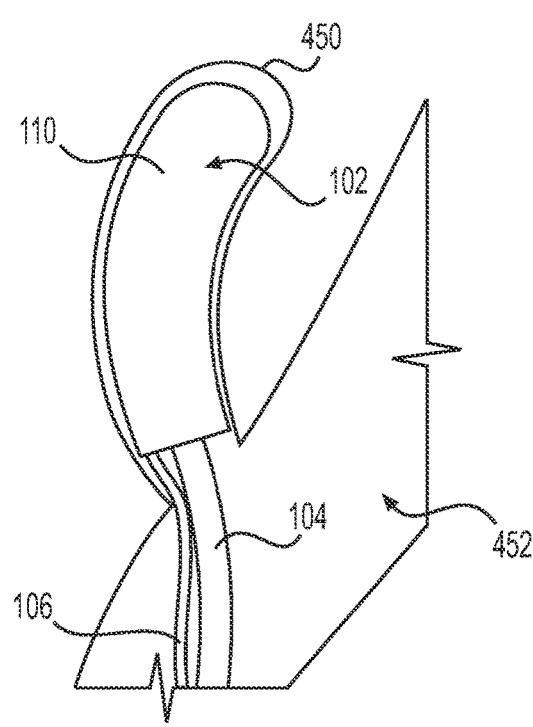

After filling wound region 450 with saline 460 and positioning rigid tool 455 abutting section 110, the user may then pull string 106 proximally to pull section 108 proximally and remove section 108 from wound region 450. FIG. 4C shows section 108 being pulled proximally out of wound region 450, and rigid tool 455 contacting section 110 to prevent proximal movement of section 110. Although FIG. 4C shows the use of rigid tool 455, a user may just pull string 106 proximally to remove section 108 without the aid of a rigid tool 455. After section 108 has been removed from the patient's body, the user may then reconnect and activate vacuum source 120 to supply negative pressure to sponge 102, and tissue of wound region 450 may be pulled towards section 110 (shown in FIG. 4D). This may allow sponge 102 to consume less space within wound region 450 and may also allow wound region 450 to continue to decrease in size as wound region 450 heals. The user may repeat these steps until central section 116 is fully exposed to wound region 450, and then the user may fully remove medical device 100 from the patient once treatment is complete. Note central section 116 may be removed from the patient's body by pulling vacuum tube 104 proximally.

When treating tissue with any of the medical devices 100, 200, 300, described herein, it may be beneficial to remove portions of sponge after a patient's tissue has developed scabbing or otherwise healed. By removing sections of a sponge 102, 202, 302, from the area of tissue with scabbing and allowing a new section of sponge (or portion of sponge that has not yet contacted tissue for treatment) to engage tissue, the tissue may heal faster.

Although FIGS. 4A-4D illustrate sponge 100 being used to treat a wound region within a patient's body, this disclosure is not so limited. Sponges 102, 202, 302 and the procedures discussed herein may be used to treat wounds, leaks, perforations, etc. in a subject's upper gastrointestinal tract, a subject's lower gastrointestinal tract, other lumens or cavities within a subject, on an exterior of a subject, etc. Various aspects discussed herein may help to reduce recovery time, reduce physician interventions, reduce a need and/or reliance on imaging or visualization to position the sponge, reduce component costs, reduce the risks to the subject, etc.

Additionally, various aspects discussed herein may be packaged as a kit to be used to treat a subject.

While principles of the disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

We claim:

1. A medical system comprising:
a delivery tube configured to couple to a vacuum source and provide negative pressure to a distal portion of the delivery tube;
a porous body at the distal portion of the delivery tube, wherein the porous body includes a first section, a second section removable from the first section, and a third section removable from the second section; and
a string coupled to the second section and the third section.

2. The medical system of claim 1, wherein the second section extends circumferentially around a radially-outermost surface of the first section, wherein the radially-outermost surface is radially-outermost from a central longitudinal axis of the porous body.

3. The medical system of claim 1, wherein the third section extends circumferentially around a radially-outermost surface of the second section, and wherein the radially-outermost surface of the second section is radially-outermost from a central longitudinal axis of the porous body.

4. The medical system of claim 1, wherein the delivery tube is coupled to a vacuum source, the porous body is cylindrical, and a central longitudinal axis of the porous body is longitudinally aligned with a central longitudinal axis of the delivery tube.

5. The medical system of claim 1, further comprising a flexible overtube coupled to the second section, wherein the delivery tube extends through a lumen of the flexible overtube.

6. The medical system of claim 1, wherein the first section is cylindrical and the second section wraps around the first section.

7. The medical system of claim 6, wherein the first section and the second section are separated by perforations.

8. The medical system of claim 1, wherein the first section is cylindrical and includes a central longitudinal axis; wherein the second section extends circumferentially around a radially-outermost surface of the first section, wherein the radially-outermost surface is radially-outermost from the central longitudinal axis of the first section; and wherein the second section is cylindrical and includes a lumen extending through the central longitudinal axis configured to receive the first section.

9. The medical system of claim 8, wherein a layer of mesh, adhesive, or agent is positioned between the first section and the second section.

10. The medical system of claim 1, further comprising a cylindrical overtube extending around the delivery tube and the porous body, wherein the overtube is configured to cover the porous body and the delivery tube.

11. The medical system of claim 1, wherein the string extends from the porous body to a proximal portion of the delivery tube, and wherein the string includes:
a first portion coupled to the second section and the third section, wherein the first portion has a length longer than a length of the delivery tube; and
a second portion coupled to the third section and extending proximally to the proximal portion of delivery tube.

12. The medical system of claim 1, wherein the first section, the second section, and the third section are concentric, and wherein the first section, the second section, and the third section have different thicknesses measured orthogonal to a central longitudinal axis of the porous body.

13. A medical device comprising:
a porous body including at least one perforation;
a negative pressure conduit having an opening formed therein that is in fluid communication with the porous body, wherein the negative pressure conduit is configured to apply a negative pressure to the porous body; and
a string coupled to the porous body and extending from the porous body to a proximal portion of the conduit, wherein the porous body is configured to separate into separate sections when the string is pulled proximally, and
wherein the string is coupled to each of the separate sections.

14. The medical device of claim 13, wherein the at least one perforation extends longitudinally along the porous body.

15. The medical device of claim 13, wherein the conduit is longitudinally aligned with a central cylindrical section of the porous body, and wherein the at least one perforation extends parallel to a longitudinal axis of the central section.

16. The medical device of claim 14, wherein the at least one perforation includes a first perforation and a second perforation; and wherein the first perforation is closer to a central longitudinal axis of the porous body than the second perforation.

17. A method of performing a medical procedure, the method comprising:
positioning a porous body adjacent to tissue of a target site;
applying a negative pressure to the porous body;
pulling a string coupled to the porous body proximally to remove a first section of the porous body while a second section of the porous body remains positioned at the target site; and
pulling the string proximally to remove the second section of the porous body,
wherein the string is coupled to each of the first section of the porous body and the second section of the porous body.

18. The method of claim 17, wherein the first section and the second section are separated by perforations.

19. The method of claim 18, wherein the perforations are configured to allow the first section to be separated from the second section when the first section is removed.

20. The method of claim 18, wherein the perforations extend longitudinally along the porous body.

\* \* \* \* \*